United States Patent [19]

Eckstein

[11] Patent Number: 4,510,311

[45] Date of Patent: Apr. 9, 1985

[54] WATER-INSOLUBLE AZOLYSTYRYL OPTICAL BRIGHTENERS

[75] Inventor: Udo Eckstein, Cologne, Fed. Rep. of Germany

[73] Assignee: Bayer Aktiengesellschaft, Leverkusen, Fed. Rep. of Germany

[21] Appl. No.: 458,085

[22] Filed: Jan. 14, 1983

[30] Foreign Application Priority Data

Jan. 30, 1982 [DE] Fed. Rep. of Germany ....... 3203058

[51] Int. Cl.³ .................. C07D 451/00; C07D 217/00; C07D 213/08; C07D 253/00
[52] U.S. Cl. ..................................... 548/132; 544/182; 544/183; 544/333; 548/131; 548/144; 548/251; 548/253; 548/254
[58] Field of Search ............... 542/456, 462, 463, 464, 542/444, 442; 548/144, 251, 254, 253, 132, 131, 133, 134, 135; 544/333, 182, 183

[56] References Cited

U.S. PATENT DOCUMENTS

| | | | |
|---|---|---|---|
| 2,901,477 | 8/1959 | Siegel et al. | 542/462 |
| 3,351,591 | 11/1967 | Siegrist et al. | 542/464 |
| 3,740,393 | 6/1973 | Bode et al. | 542/463 |
| 3,796,705 | 3/1974 | Siegrist | 542/463 |
| 4,113,937 | 9/1978 | Siegrist et al. | 542/462 |
| 4,113,938 | 9/1982 | Siegrist et al. | 542/464 |
| 4,138,552 | 2/1979 | Schläpfer-Illi | 542/462 |
| 4,246,403 | 1/1981 | Prossel et al. | 548/144 |
| 4,323,675 | 4/1982 | Eckes et al. | 548/131 |

FOREIGN PATENT DOCUMENTS

| | | |
|---|---|---|
| 0006171 | 1/1980 | European Pat. Off. . |
| 0009095 | 4/1980 | European Pat. Off. . |
| 0022491 | 1/1981 | European Pat. Off. . |
| 1955065 | 5/1971 | Fed. Rep. of Germany . |

OTHER PUBLICATIONS

Journal of the American Chemical Society, vol. 80, 1958, Easton, W. G. Finnegan et al., "An Improved Synthesis of 5-Substituted Tetrazoles", pp. 3908–3911.

*Primary Examiner*—Donald G. Daus
*Assistant Examiner*—Cecilia Shen
*Attorney, Agent, or Firm*—Sprung Horn Kramer & Woods

[57] ABSTRACT

The invention relates to compounds of the formula

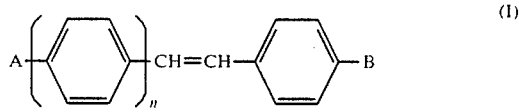

or isomeric mixtures thereof, wherein
A represents a quasiaromatic heterocyclic radical,
B represents a radical of the formulae

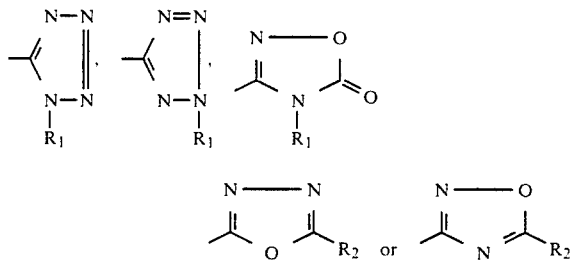

n represents 0, 1, 2 or 3, preferably 0–2,
$R_1$ represents hydrogen, CN, R or acyl,
$R_2$ represents hydrogen, halogen, —OR, —NHR, —N(R')$_2$ or NHCOR,
R' represents alkyl and
R represents R', alkenyl, aralkyl, cycloakyl or aryl.

They are valuable optical brighteners and/or laser dyes and some of them are intermediate products for preparing these end products.

8 Claims, No Drawings

WATER-INSOLUBLE AZOLYSTYRYL OPTICAL BRIGHTENERS

The invention relates to compounds of the formula

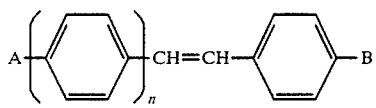

or isomeric mixtures thereof,
wherein
A represents a quasiaromatic heterocyclic radical,
B represents a radical of the formulae

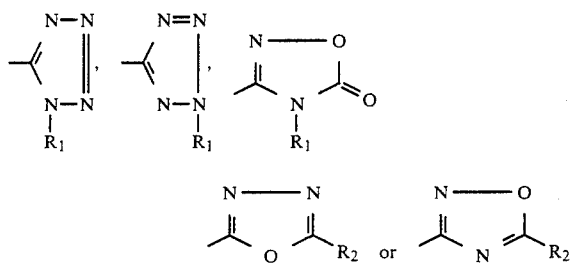

n represents 0, 1, 2 or 3, preferably 0–2,
$R_1$ represents hydrogen, CN, R or —$SO_2R$, —COR, COOR, —CONHR or —CON(R')$_2$,
$R_2$ represents hydrogen, halogen, —OR, —NHR; —N(R')$_2$ or NHCOR,
$R^1$ represents alkyl and
R represents $R^1$, alkenyl, aralkyl, cycloalkyl or aryl, wherein A, B, R' and R can carry further non-chromophoric substituents which are customary in the chemistry of optical brighteners or laser dyes.

Suitable quasiaromatic heterocyclic radicals A are radicals of 5-membered or 6-membered 1-nuclear to 3-nuclear heterocyclic compounds such as for example those of the oxazole, imidazole, 1,2,4-oxadiazole, 1,3,4-oxadiazole, 1,3,4-thiadiazole, 1,2,3-, 1,2,4- and 1,3,4-triazole, pyrimidine, 1,3,5-triazine, benzoxazole, benzothiazole, benzimidazole, naphthoxazole, benzo-s-triazole, naphtho-s-triazole, benzo (b)-furan, quinazoline, or quinoxaline series, which are linked in a customary manner with the remaining molecule radical.

Those of the benzoxazole, benzo(b)furan, benzo-s-triazole, naphtho-s-triazole, 1,2,4- and 1,3,4-oxadiazole, 1,2,3-, 1,2,4- and 1,3,4-triazole and 1,3,4-triazine series are particularly preferred.

Suitable non-chromophoric substituents are R, OH, CN, OR, COR, $SO_2R$, NHCOR, $CONH_2$, $NHSO_2R$, OCOR, COOR, COOH, NHR', $SO_3H$ and others.

Alkyl is in particular $C_1$–$C_6$-alkyl, which can be substituted by hydroxyl, $C_1$–$C_4$-alkoxy, CN, carboxyl, $C_1$–$C_4$-alkoxycarbonyl, $CONH_2$, chlorine or bromine, or trifluoromethyl.

Alkenyl is in particular $C_2$–$C_5$-alkenyl.

Halogen is in particular fluorine, chlorine and bromine, preferably chlorine.

Cycloalkyl is preferably cyclohexyl which can be mono- to tri-substituted, for example by methyl or chlorine.

Aryl is in particular phenyl which is optionally substituted by $C_1$–$C_4$-alkyl, trifluoromethyl, chlorine, bromine, carboxyl, cyano, $C_1$–$C_4$-alkoxycarbonyl or $C_1$–$C_4$-alkoxy.

Aralkyl is in particular phenyl-$C_1$–$C_4$-alkyl which can also be substituted in the phenyl nucleus by chlorine, methyl or methoxy.

Preferred compounds are those of the formula I, wherein

A represents a 1,2,4-oxadiazole, 1,3,4-oxadiazole or 1,2,3-triazole radical or a benzoxazole, benzo(b)furan, benzo-s-triazole, naphtho-s-triazole, 5-phenyl-1,3,4-oxadiazole, 5-phenyl-1,2,4-oxadiazole, or 3-phenyl-1,2,4-oxadiazole radical which is optionally substituted by 1 or 2 $C_1$–$C_4$-alkyl, $C_1$–$C_4$-alkoxy, 1 or 2 chlorine, benzyl, phenyl, cyclohexyl, $C_1$–$C_4$-alkylsulphonyl or $C_1$–$C_4$-alkoxycarbonyl, and B represents a radical of the formula

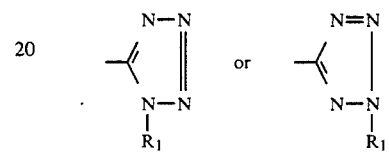

(or mixtures of the two),
wherein
$R_1$ denotes hydrogen, allyl, $C_1$–$C_4$-alkoxycarbonyl, an alkyl radical which is optionally substituted by hydroxyl, acetoxy, $C_1$–$C_4$-alkoxy, phenoxy, chlorine, cyano, sulpho or $CF_3$— or a benzyl or benzoyl radical which is optionally substituted by $C_1$–$C_4$-alkyl, $C_1$–$C_4$-alkoxy, $C_1$–$C_4$-alkoxycarbonyl, cyano or chlorine.

Particularly preferred radicals A are the benzoxazolyl-2, benzo(b)furanyl, 1,2,4 or 1,3,4-oxadiazolyl, naphtho-triazolyl and the benzo-s-triazol-2-yl radical.

A further group of preferred compounds are those of the formula I, wherein
A has the above-mentioned preferred meaning and
B represents a radical of the formula

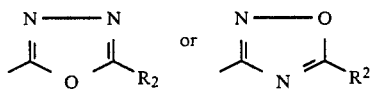

wherein
$R_2$ denotes hydrogen, chlorine, amino, $C_1$–$C_4$-alkylamino, phenylamino or a radical of the formula —(OCH$_2$CH$_2$)$_m$—OW W denotes hydrogen, $C_1$–$C_6$-alkyl which is optionally substituted by chlorine or cyano, benzyl, cyclohexyl or phenyl and
m denotes an integer of from 0 to 7.

A further group of preferred compounds are those of the formula I, wherein
A has the above-mentioned preferred meaning and
B represents the radical of the formula

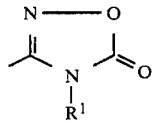

wherein $R_1$ denotes hydrogen, $C_1$–$C_4$-alkyl, which is optionally substituted by hydroxy, $C_1$–$C_4$-alkoxy, chlorine, cyano, $C_1$–$C_4$-alkoxycarbonyl or phenyl, Particularly preferred compounds are those of the formula (I), wherein A represents the radical of the formula

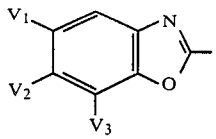

and

B represents the radical of the formulae

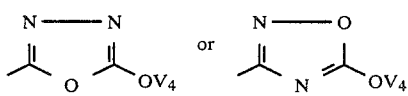

wherein n = 1 and wherein $V_1$ denotes hydrogen, $C_1$–$C_4$-alkyl, cyclohexyl, $C_1$–$C_4$-alkoxy, chlorine, benzyl, phenyl, $C_1$–$C_4$-alkoxycarbionyl or $C_1$–$C_4$-alkylsulphonyl, $V_2$ denotes hydrogen, $C_1$–$C_4$-alkyl, chlorine or $C_1$–$C_4$-alkoxy, $V_3$ denotes hydrogen, $C_1$–$C_4$-alkyl or chlorine and $V_4$ denotes $C_1$–$C_6$-alkyl which is optionally substituted by $C_1$–$C_4$-alkoxy, hydroxyl, chlorine or cyano; benzyl, cyclohexyl or phenyl.

$V_4$ very particularly preferably represents an unsubstituted $C_1$–$C_4$-alkyl radical such as methy, ethyl, n-propyl, isopropyl or n-butyl; $V^1$ very particularly preferably represents hydrogen, methyl or chlorine; and $V^2$ and $V^3$ very particularly preferably represent hydrogen.

The compounds of the formula (I) can be prepared according to various methods known per se. Preferably (a) a phosphono compound of the formula

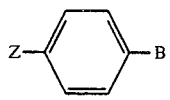

wherein

Z represents a grouping of the formula

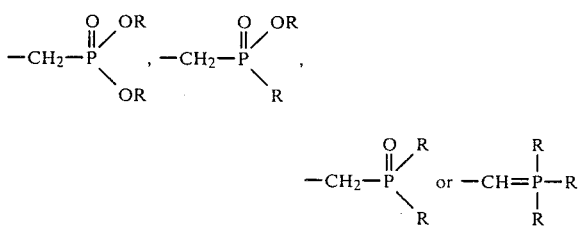

is subjected to a condensation reaction with an aldehyde of the formula

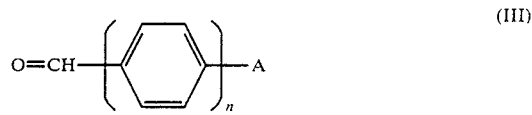

or (b) a phosphono compound of the formula

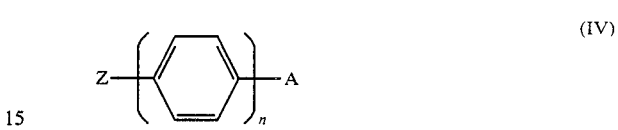

is subjected to a condensation reaction with an aldehyde of the formula

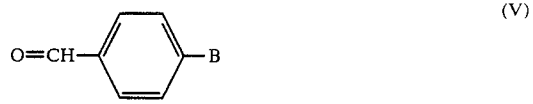

in organic solvents in the presence of basic condensation agents, cf. for example DE-OS (German Offenlegungsschriften Nos. 2,525,684, 2,833,470 and 3,013,279).

Preferred radicals R are $C_1$–$C_4$-alkyl, cyclohexyl or phenyl.

Inert solvents, for example, hydrocarbons such as toluene or xylene or alcohols such as methanol, ethanol, isopropanol, butanol, glycol, glycol ethers such as 2-methoxy-ethanol, hexanol, cyclohexanol, cyclooctanol, also ethers such as diisopropylether, dioxane, tetrahydrofuran, and furthermore formamides or N-methylpyrrolidone are advantageously chosen as solvents. Dipolar aprotic solvents such as dimethyl formamide and dimethyl sulphoxide are particularly suitable.

Possible condensation agents are strongly basic compounds such as alkali metal and alkaline earth metal hydroxides, alkali metal and alkaline earth metal amides and alkali metal and alkaline earth metal alcoholates, for example potassium hydroxide, sodium hydroxide, potassium tert.-butylate, sodium amide or sodium methylate, also the alkali metal compounds of dimethyl sulphoxide and alkali metal hydrides as well as optionally, alkali metal dispersions.

The reaction is preferably carried out in the temperature range of 0° to 100° C.

The compounds of the formula I according to the invention can also be prepared in such a manner that the corresponding aldehyde anils are reacted with the corresponding methyl compounds in a dipolar aprotic solvent, such as dimethyl formamide in the presence of basic condensation agents.

While the compounds III and IV are generally known (cf. DE OS Nos. 1,224,917, 2,148,014, 2,453,355, 2,709,924 and 2,926,234 and U.S. Pat. Nos. 3,351,591 and 4,142,044) the compounds of the formulae II and V ($R_1$/$R_2$≠hydrogen) have hitherto not been described in the literature; these compounds are obtained in a manner known per se according to the following reaction equation:

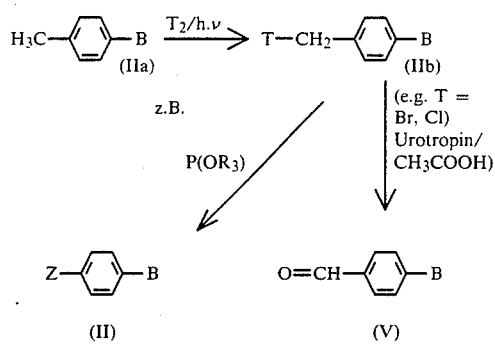
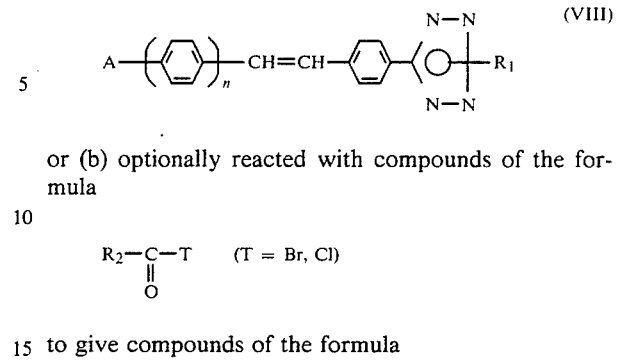

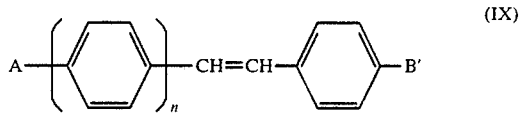

or (b) optionally reacted with compounds of the formula $$R_2-\underset{\underset{O}{\|}}{C}-T \quad (T = Br, Cl)$$

to give compounds of the formula

wherein

B' represents

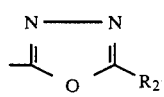

In this method of preparation the compounds VIII, depending on the reaction conditions, can also be produced in the form of isomeric mixtures which, if desired, can be separated by customary separation methods (recrystallization, chromatography).

However, for the industrial purposes mentioned further below such separation is not necessary.

Only some of the compounds of the formula (VI are known. They are obtained in a customary manner, e.g. by reacting compounds of the formula

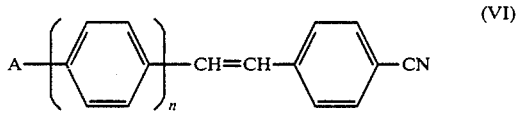

with p-cyanobenzaldehyde (cf. DE-OS 2,453,355, DE-AS (German Auslegeschrift) No. 1,052,405, JP-OS (Japanese Laid-open Specification) No. 49/95378).

The reaction of the tetrazole derivatives VII with the compounds R₁X can be carried out in the temperature range of 0°–120° C., preferably at 25°–90° C. and the reaction of VII with R₂COT in the range of 50°–150° C., preferably at 70°–120° C.

Both reactions are carried out in inert solvents, for example ethers such as dioxane, tetrahydrofuran, diisopropyl ether, also in hydrocarbons such as toluene, xylene, chlorobenzene and 1,2-dichlorobenzene or in formamides such as dimethylformamide, dimethyl acetamide or dimethyl sulphoxide, preferably in the presence of acid acceptors, in particular tertiary organic bases such as triethylamine, dimethyl aniline, pyridine, dimethyl aniline, or hexahydro-dimethylaniline.

A particular process for the preparation of compounds of the formula I, wherein B represents the radical of the formula The starting compounds (IIa) (B=a 1,2,3,4-tetrazole radical) can be prepared by known methods by cycloaddition of sodium azide on to p-tolunitrile and subsequent reaction of the product with corresponding halides (cf. for example J. org. Chem. 15, 1082 (1950), J. Org. Chem. 22, 1142 (1957), J. Amer. Chem. Soc. 80, 3908 (1958) and Can. Journal of Chem. 47, 813 (1969).

The educts (IIa) (B=a 1,3,4-oxidiazole radical) can be prepared according to various processes known in the literature (cf. for example Gazz. chim. ital, 91, 866 (1961); Tetrahedron Letters 42 (1964) 3119 and Ann. 686 (1965) 145).

The condensation of amidoxims with chloroformic acid esters (cf. Ber. 18, 2465 (1885) and Ber. 19, 1481 (1886) as well as Ber. 182456 (2885) and Ber. 19, 1475 (2886) and the subsequent reaction of the products with corresponding halides in the presence of basis produces the educts (IIa) or even directly (II) (B=1,2,4-oxadiazolinone-2 radical).

Finally the educts (IIa) (B=1,2,4-oxadiazole radical) are obtained in a manner known per se from the unsubstituted oxadiazolinone-2 compounds by chlorination and reaction with alcohols or amines (cf. for example Bull. Soc. Chim. Belges 78 (1969) 41 and Bull. Soc. Chim. Belges 78, 47 (1969).

A particularly advantageous process for preparing compounds of the formula (I) is characterised in that compounds of the formula

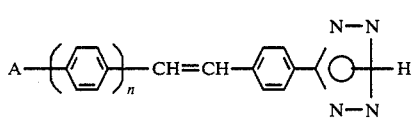

are reacted with metal azides in polar organic solvents to give compounds of the formula

and this is either (a) optionally reacted with compounds of the formula

R₁—X wherein

X represents halogen, to give compounds of the formula

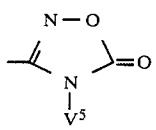

is characterised in that compounds of the formula I, wherein
B represents the radical of the formula

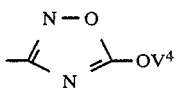

are rearranged in a polar solvent, either in the presence of auxiliaries such as for example acids or bases or however, without auxiliaries at temperatures of between 100°–250° C. The compounds of the formula I are obtained in good yields and with a high purity.

The preparation of the compounds of the formula I wherein $V^5$=hydrogen can finally also be conducted by reacting the compounds of the formula I, wherein $V^4$=$C_1$–$C_4$-alkyl, with mineral acids in organic solvents.

The bases which can be used in the process according to the invention are both inorganic and organic compounds which are sufficiently soluble in the reaction mixture. Preferred bases are organic bases, such as for example, triethylamine, N-methyl or N-ethylpiperidine, piperidine, pyrrolidine, 1,4-diazobicyclo[2,2,2]octane (DABCO), morpholine, N-methyl or N-ethyl morpholine and N-ethyl pyrrolidine or the like.

Suitable polar solvents are higher-boiling alcohols such as n-butanol, tert.-butanol, glycol and diethylene glycol. Glycolethers such as 2-methoxyethanol, 2-ethoxyethanol, nitriles such as for example, benzonitrile, also formamides, N-methyl pyrrolidone, dimethyl sulphoxide and phosphoric acid amides. Dimethyl formamide, dimethyl acetamide and phosphoric acid tris-dialkylamides in which alkyl is in particularl $C_1$–$C_4$-alkyl, are preferred.

The reaction temperatures for the reaction according to the invention are approximately between 100° and 250° C., preferably between 120° and 200° C.

The brightening of the fibre material with the aqueous or possibly organic brightener liquor is carried out by the dyeing process typical for the type of fibre concerned.

The reaction products of the above processes can be subjected to even further known transformation such as halogenation, functional modifications of carboxyl groups, the introduction of chloromethyl groups or the replacement of halogen atoms with cyano groups.

The compounds of the formula I exhibit a very intense blue fluorescence in a dissolved or finely divided state. They are suitable by themselves or in the form of mixtures for whitening the most diverse organic material.

The following materials may be mentioned as examples of substrates to be brightened: lacquers, natural or synthetic fibres, such as for example those of natural or regenerated cellulose, acetyl cellulose, natural and synthetic polyamides, polyesters, polyolefins, polyvinyl chloride, polyvinylidene chloride, polystyrene or polyacrylonitrile as well as foils, films, tapes or moulded articles of such materials.

The water-insoluble compounds according to the invention can be used dissolved in organic solvents or in an aqueous dispersion, advantageously with the aid of a dispersion medium.

The quantity of the compounds of the general formula I to be used according to the invention, based on the material to be optically brightened, can vary within wide limites, depending on the field of application and the desired effect. It can easily be determined by tests and is in general between about 0.01 and about 2%.

Compounds of the formula (I) in particular those of the formula I with an oxdiazolyl radical are, with their high quantum yield and high light fastness values, also furthermore, able to be used for tunable dye laswers in the blue spectral range of 400–480 nm. For this purpose they are used according to the instructions described in DE OS No. 1,910,784 or GB PS No. 1,255,399.

EXAMPLE 1

A suspension of 51.5 g (0.16 mol) of 4-cyano-4'-(benzoxazole-2"-yl)-stilbene, 11.4 g (0.175 mol) of sodium azide and 7.4 g (0.175 mol) of lithium chloride in 850 ml of dimethyl formamide are stirred for 25 hours at 130° C. The mixture is adjusted with concentrated hydrochloric acid to pH 3–4 and filtered. Washing the filtrate with water and ethanol yields, after drying the product in vacuo at 50° C., 60.6 g (94.8% of theory) of the compound of the formula

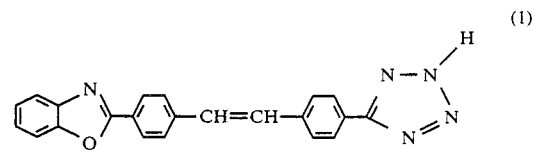

which can be recrystallised from dimethyl acetamide (melting point: 321° C. with decomposition, λmax. 369 nm).

EXAMPLE 2

5.2 g (0.03 mol) of benzyl bromide are added at 60° C. within 15 minutes to a solution of 11 g (0.03 mol) of compound (1) from example 1 and 3.3 g (0.033 mol) of triethylamine in 120 ml of dimethyl formamide and the mixture is subsequently stirred for 3 hours at 90° C. After cooling the reaction mixture to 25° C. 300 ml of water are added and the crystalline precipitate is filtered off. 8.5 g (62% of theory) of a 1,2-isomer mixture of the formula

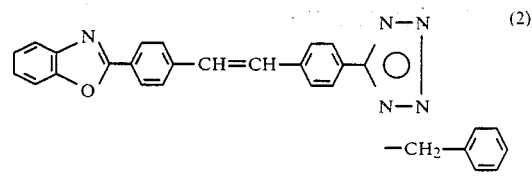

which can be recrystallized from dimethyl formamide (melting point: 249°–51° C., $\lambda_{max}$: 360 nm) are obtained. The compound produces excellent brightening effects on PES (polyester) in the high temperature exhaustion process (130° C.).

The compounds listed in the following table are also prepared analogously to the above example

| | A-⟨phenyl⟩-CH=CH-⟨phenyl⟩-C(tetrazole)-R | | |
|---|---|---|---|
| No. | A | R | Fluorescence in DMF* |
| 3 | ⟨naphtho-triazole: naphthalene fused with N=N-N ring, connected via N⟩ | H(2-) | greenish-tinged blue |
| 4 | ⟨5-Cl-benzoxazol-2-yl⟩ Cl | H(2-) | blue violet |
| 5 | ⟨5-Cl-benzoxazol-2-yl⟩ Cl | CH₂—⟨C₆H₄⟩—OCH₃ | reddish-tinged blue |
| 6 | CH₃OOC—⟨benzoxazol-2-yl⟩ | H(2-) | blue |
| 7 | C₂H₅OOC—⟨benzoxazol-2-yl⟩ | CH₂CH₂—CN | red violet |
| 8 | CH₃O—⟨benzoxazol-2-yl⟩ | —CH₂—CH=CH₂ | neutral blue |
| 9 | Ph—⟨triazole, NH⟩ | —C(=O)—OC₂H₅ | greenish-tinged blue |
| 10 | Ph, CH₃—⟨triazole⟩ | —C(=O)—⟨C₆H₅⟩ | blue-violet |
| 11 | C₂H₅SO₂—⟨benzoxazol-2-yl⟩ | —C(=O)—N(C₂H₅)₂ | greenish-tinged blue |
| 12 | ⟨biphenyl-oxadiazol-2-yl⟩ | H(2-) | blue |
| 13 | CH₃—⟨benzofuran-2-yl⟩ | H(2-) | reddish-tinged blue |

EXAMPLE 14

11 g (0.03 mol) of the compound (1) from example 1 and 7.1 g (0.07 mol) of triethylamine are stirred in 100 ml of dimethylformamide for one hour at 80° C. 3.3 g (0.03 mol) of chloroformic acid ethyl ester are then added dropwise below the surface of the solution. The mixtur is stirred for 2 hours at 80° C. and once again treated with 3.3 g (0.03 mol) of chloroformic acid ethyl ester. After 2 hours at about 90° C. the mixture is cooled to 10° C. and filtered to separate non-converted starting product. The filtrate is concentrated in vacuo, the residue is treated with 50 ml of water and filtered off. Drying the filtrate in vacuo at 50° C. yields 8.5 g (69.1% of theory) of light yellow crystals of the compound of the formula

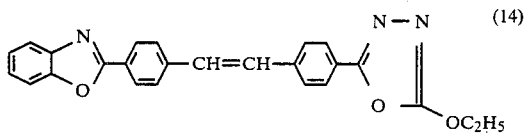

which can be recrystallized from chlorobenzene. Melting point 209°–211° C., absorption: $\lambda_{max}$: 364 nm. It produces brilliant brightening effects on PES in the high temperature exhaustion and thermosol process.

EXAMPLE 15

Following the same procedure as in Example 14 the reaction of compound (3) with chloroformic acid methyl ester produces 9.2 g (68.8% of theory) of the compound of the formula

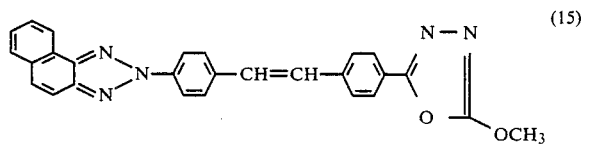

in the form of yellow crystals which can be recrystallized from 1,2-dichlorobenzene (melting point 229°–32° C.; fluorescence in DMF: $\lambda_{max}$: 372 nm).

EXAMPLE 16

16.6 g of triethyl phosphite are added dropwise at 100° C. under nitrogen solution of 22.7 g (0.08 mol) of 5-ethoxy-2-(4'-bromomethylphenyl)-1,3,4-oxadiazole in 80 ml of toluene in such a manner that the bromoethane produced immediately distils off. The mixture is stirred for 4 hours at about 110° C. and the toluene and excess triethyl phosphite are removed in vacuo. 100 ml of dimethyl formamide and 19 g (0.08 mol) of 2-(4'-formyl-phenyl)-5-methyl-benzoxazole are added to the residue. 100 ml (0.1 mol) of a 1 molar sodium methylate solution are added dropwise at 50° C. to the mixture which is then stirred for 4 hours at 60° C. The mixture is cooled to room temperature, neutralised with 6.6 g (0.11 mol) of glacial acetic acid and 100 ml of ethanol are added. Filtering off the mixture, washing the filtrate with ethanol and drying the product in vacuo at 50° C. gives 20.1 g (59.5% of theory) of a very clean crude product of the formula

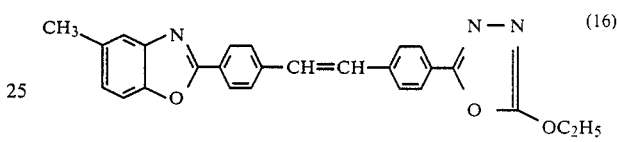

which is recrystallized from xylene (melting point: 215° C., $\lambda_{max}$: 366 nm). The compound produces excellent brightening effects on PES with very good fastness values.

2-(4'-bromo-methylphenyl)-5-ethoxy-1,3,4-oxadiazole is prepared in a known manner from the corresponding tolyl compound by bromination with N-bromosuccinimide in carbon tetrachloride.

In an analogous manner to that described in Examples 14–16 the following compounds are also prepared:

| No. | A | Q | Fluorescence in DMF |
|---|---|---|---|
| 17 | 5-CH₃, 7-CH₃ benzoxazolyl | —OCH₃ | blue |
| 18 | 5-CH₃, 6-CH₃ benzoxazolyl | —OC₂H₅ | neutral blue |
| 19 | 5-C(CH₃)₃ benzoxazolyl | —OCH₂CH₂OCH₃ | neutral blue |

-continued structure: A—C6H4—CH=CH—C6H4—C(=N-N)—O—Q (oxadiazole)

| No. | A | Q | Fluorescence in DMF |
|---|---|---|---|
| 20 | naphtho[1,2-d]-1,2,3-triazol-2-yl | —OC4H9 | blue |
| 21 | 2H-benzotriazol-2-yl | —OCH2CH2Cl | neutral blue |
| 22 | 4-phenyl-2H-1,2,3-triazol-2-yl | —OCH2—C6H5 | reddish-tinged blue |
| 23 | 2-(4-methoxyphenyl)-1,3,4-oxadiazol-5-yl | —OCH3 | blue |
| 24 | 5-methoxybenzoxazol-2-yl | —OCH3 | intensive blue |
| 25 | 5-(methoxycarbonyl)benzoxazol-2-yl | —OCH(CH3)2 | violet blue |
| 26 | naphtho[1,2-d]-1,2,3-triazol-2-yl | —OCH2CH2OC2H5 | blue |
| 27 | benzofuran-2-yl | N(CH3)2 | greenish-tinged blue |
| 28 | 5,7-dichlorobenzoxazol-2-yl | —NH2 | greenish-tinged blue |
| 29 | 4-phenyl-5-methyl-2H-1,2,3-triazol-2-yl | —NH—C6H5 | bluish-tinged green |

EXAMPLE 30

20 g (0.11 mol) of 30% strength sodium-methylate solution are added dropwise at 50° C. within 30 minutes to a suspension of 13.7 g (0.05 mol) of 2-(4-formyl-phenyl)-naphth[1,2-d]-1,2,3-triazole and 15.6 g (0.05 mol) of 3-(4-diethoxyphosphonomethyl-phenyl)-1,2,4-oxadiazole-5-one in 150 ml of anhydrous dimethyl-formamide. The mixture is stirred for 3 hours at 50°–60° C.

and then 20 g of concentrated, acetic acid are added. After the mixture has been cooled it is filtered off and the filtrate washed successively with 50 ml each of 5% strength hydrochloric acid, water and methanol. Drying the product in vacuo at 50° C. gives 13.6 g (63% of theory) of a light yellow crystal powder of the compound of the formula

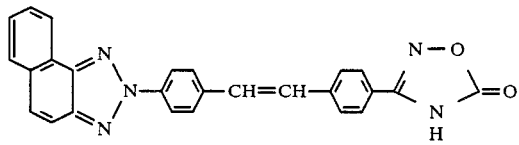
(30)

which can be recrystallized from dimethyl formamide. Melting point: >300° C., IR (KBr): 3430 cm$^{-1}$, 1760 cm$^{-1}$, 1599 cm$^{-1}$, UV-absorption (DMF): $\lambda_{max.}$=374 nm.

The diethoxy-phosphono-methyl compound used, of the formula

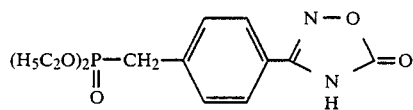

is prepared in the following manner:

28 g (0.4 mol) of hydroxylamine hydrochloride and 20 g (0.2 mol) of sodium carbonate are dissolved in 300 ml of distilled water. 27.8 g (0.11 mol) of 4-(diethoxy-phosphonomethyl)-benzonitrile are added dropwise to the solution and the mixture is stirred for 2 hours at 80° C. After cooling the mixture to room temperature it is extracted three times, each time with 100 ml of chloroform and the combined chloroform phases are dried over anhydrous sodium sulphate. The solvent is removed in vacuo and the crude oil obtained is dissolved in 100 ml of anhydrous xylene. 17.8 g (0.11 mol) of pyrocarbonic acid ethyl ester are added and the interior temperature is increased slowly, ethanol being first of all distilled off and later xylene (about 2-3 hours). After the reaction has ended half of the solvent is removed by distillation and cooled. Filtering off the product and drying the filtrate in vacuo at 50° C. yields 26.2 g (76.3% of theory) of colourless crystals with a melting point of 196°-201° C. which can be recrystallized from ethanol.

| $C_{13}H_{17}N_2O_5P(312,3)$ | C % | H % | N % |
|---|---|---|---|
| calculated: | 50,0 | 5,49 | 8,97 |
| found: | 49,9 | 5,4 | 8,6 |

EXAMPLE 31

11.2 g (0.05 mol) of 2-(4-formyl-phenyl)-benzoxazole and 15.6 g (0.05 mol=of 3-(4-diethoxy-phosphonomethylphenyl)-1,2,4-oxadiazolin-5-one are suspended in 100 ml of anhydrous dimethyl formamide and the reaction and isolation are carried out in the same way as described in Example 30.

15.2 g (79.7% of theory) of light yellow crystals of the compound of the formula

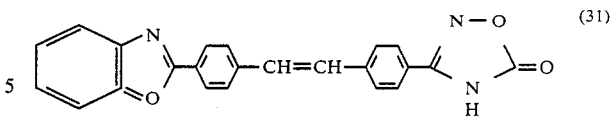
(31)

are obtained which can be recrystallized from dimethylformamide. Melting point: >300° C.; IR (KBr): 3425 cm$^{-1}$, 1760 cm$^{-1}$, 1605 cm$^{-1}$; UV-absorption (in DMF) $\lambda_{max}$=362 nm.

EXAMPLE 32

Following the same procedure as in Example 30, 16.5 g (75.1% of theory) of light yellow crystals of the compound of the formula

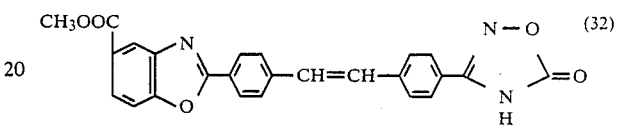
(32)

which can be recrystallized from dimethyl acetamide are obtained from 14.1 g (0.05 mol) of 2-(4-formyl-phenyl)-5-carbomethoxy-benzoxazole and 15.6 g (0.05 mol) of 3-(4-diethoxy-phosphonomethyl-phenyl)-1,2,4-oxadiazolin-5-one. M.p. >300° C.; IR (KBr) 3420 cm$^{-1}$, 4765 cm$^{-1}$, 1735 cm$^{-1}$, 1600 cm$^{-1}$; UV-absorption (in DMF) $\lambda_{max}$=364 nm.

EXAMPLE 33

8.63 g (0.02 mol) of the compound (30) are suspended in 100 ml of anhydrous dimethyl formamide and 4 g (0.022 mol) of 30% strength sodium methylate solution are added. After stirring for 1 hour at 50° C. 3.74 g (0.022 mol) of 2-iodopropane are added dropwise and the reaction mixture is stirred for 4 hours at 80° C. The reaction mixture is filtered off at 50° C. the filtrate is concentrated to dryness and treated with 50 ml of water and 10 g of concentrated acetic acid. Filtering off the product and drying the filtrate in vacuo at 50° C. yields 6.1 g (64.4% of theory) of a yellow crystal powder of the compound of the formula

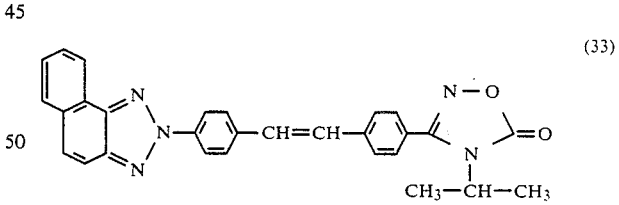
(33)

which can be recrystallized from dimethylacetamide (UV-absorption (DMF): $\lambda_{max}$=372 nm; IR (KBr): 3430 cm$^{-1}$; 1775 cm$^{-1}$, 1605 cm$^{-1}$).

EXAMPLE 34

20 g (0.11 mol) of 30% strength sodium methylate solution are added dropwise at 50° C. within 30 min to a suspension of 11.9 g (0.05 mol) of 2-(4-formyl-phenyl)-5-methyl-benzoxazole and 15.6 g (0.05 mol) of 3-(4-diethoxy-phosphonomethyl-phenyl)1,2,4-oxadiazolin-5-one in 100 ml of anhydrous dimethyl formamide. The mixture is stirred for about 3 hours at 50°-60° C. until the reaction is complete. Then 8.4 g (0.055 mol) of α-bromo-acetic acid methyl ester are added and the mixture is stirred for 3 hours at 90° C. After the mixture has cooled to room temperature 20 g of concentrated acetic acid are added, the yellow precipitate is filtered off, the filtrate is washed with water and methanol and dried in vacuo at 50° C. Yield: 15.3 g (65.4% of theory) of the compound of the formula

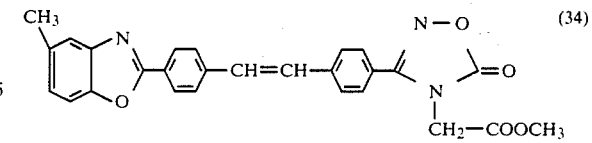
(34)

which can be recrystallized from methyl glycol (UV-absorption (DMF: $\lambda_{max}=364$ nm). In the same way as described in examples 30–34 the following compounds are also prepared:

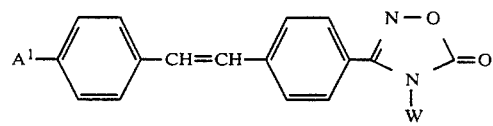

| No. | A₁ | W | Fluorescence in DMF |
|---|---|---|---|
| 35 | benzoxazol-2-yl | —CH₂—COOC₂H₅ | reddish-tinged blue |
| 36 | 5-methoxy-benzoxazol-2-yl | H | red-violet-blue |
| 37 | 5-methoxy-benzoxazol-2-yl | CH₃ | reddish-tinged blue |
| 38 | 5,7-dimethyl-benzoxazol-2-yl | —C₄H₉ | blue |
| 39 | 5-chloro-benzoxazol-2-yl | —CH₂—phenyl | very reddish-tinged blue |
| 40 | 2H-benzotriazol-2-yl | —CH₂—CH=CH₂ | neutral blue |
| 41 | 5-methoxy-2H-benzotriazol-2-yl | H | slightly greenish tinged blue |
| 42 | 4-methyl-5-phenyl-triazol-yl | H | blue |

-continued $$A^1-\!\!\bigcirc\!\!-CH=CH-\!\!\bigcirc\!\!-\overset{N-O}{\underset{\underset{W}{N}}{\diagdown}}\!\!=\!O$$

| No. | A₁ | W | Fluorescence in DMF |
|---|---|---|---|
| 43 | CH₃-triazole-phenyl | H | blue |
| 44 | H-triazole-phenyl | —CH(CH₃)₂ | reddish-tinged blue |
| 45 | naphtho-triazole | CH₂—COOC₂H₅ | very strong blue |
| 46 | phenyl-oxadiazole | H | reddish-tinged blue |
| 47 | biphenyl-oxadiazole | C₂H₅ | blue |
| 48 | CH₃O-phenyl-oxadiazole | —C₂H₅ | blue violet |

EXAMPLE 49

20 g of triethylphosphite are added dropwise at 100° C. under nitrogen to a solution of 22.7 g (0.08 mol) of 5-ethoxy-3-(4-bromoethyl-phenyl)-1,2,4-oxadiazole in 80 ml absolute toluene, in such a manner that the bromoethane produced distils off immediately. The mixture is stirred for 5 hours at about 100° C. and the toluene and excess triethyl phosphite are removed in vacuo. 100 ml of dimethyl formamide and 21.9 g (0.08 mol) of 2-(4-formyl-phenyl)-naphth[1,2-d]-1,2,3-triazole are added to the residue. At 50° C. 100 ml (0.1 mol) of a 1 molar sodium methylate solution are added dropwise to the mixture which is then stirred for 4 hours at 50°–60° C. The mixture is cooled to room temperature, neutralised with 6.6 g (0.11 mol) of glacial acetic acid and filtered off. Washing the filtrate with ethanol and drying in vacuo at 50° C. yields 23.0 g (62.5% of theory) of yellow crystals of the compound of the formula

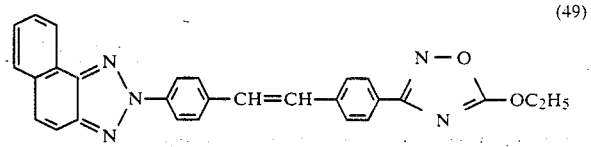
(49)

which can be recrystallized from chlorobenzene (UV-absorption (in DMF) λ_max=370 nm). 5-ethoxy-3-(4-bromomethyl-phenyl)-1,2,4-oxadiazole is obtained from 3-(4-methyl-phenyl)1,2,4-oxadiazole (cf. F. Eloy, A. Deryckere, A. van Overstraeten Bull. Soc. Chim. Belges 78 (1969) 47–54) in a known manner by bromination with N-bromo succinimide in carbon tetrachloride.

EXAMPLE 50

15.5 g (75.6% of theory) of the compound of the formula

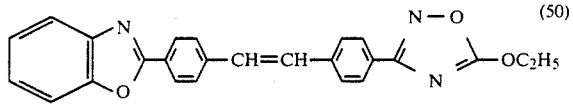

(50)

which is recrystallized from chlorobenzene (UV-absorption (in DMF) $\lambda_{max}=360$ nm are obtained from 11.2 g (0.05 mol) of 2-(4-formyl-phenyl)-benzoazole and 14.2 g (0.05 mol) of 5-ethoxy-3-(4-bromomethylphenyl)-1,2,4-oxadiazole.

In an analogous manner the following compounds are also prepared:

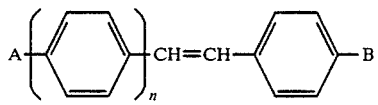

| No. | A² | Q¹ | Fluorescence in DMF |
|---|---|---|---|
| 51 | (benzotriazole) | —OCH₃ | intense blue |
| 52 | CH₃O-(benzotriazole) | —OCH₃ | slightly greenish-tinged blue |
| 53 | (naphthotriazole) | —OCH₂CH₂—OCH₃ | strong blue violet |
| 54 | (naphthotriazole) | —OC₄H₉—n | blue violet |
| 55 | (benzoxazole) | —OCH₂—phenyl | reddish-tinged blue |
| 56 | CH₃-(dimethylbenzoxazole)-CH₃ | —OC₃H₇—i | blue |
| 57 | (benzoxazole) | —NH—phenyl | greenish-tinged blue |

EXAMPLE 58

14.5 g (0.03 mol) of compound 49 are heated with refluxing in 100 ml of dimethyl formamide for 3 hours. After cooling to room temperature 50 ml of methanol are added and the precipitated product is filtered off, washed with methanol and dried in vacuo at 50° C.

11 g/75.9% of theory) of the compound of the formula

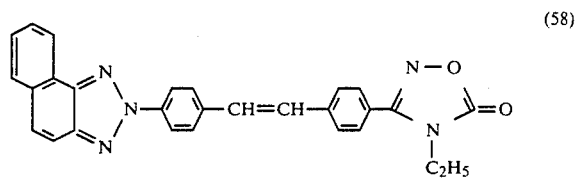

(58)

are obtained, which is recrystallized from dimethyl acetamide (UV-absorption (in DMF): $\lambda_{max}=373$ nm).

I claim:

1. A water-insoluble compound of the formula

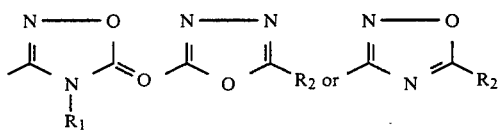

wherein

A is an oxazole, imidazole, 1,2,4-oxadiazole, 1,3,4-oxadiazole, 1,3,4-thiadiazole, 1,2,3-, 1,2,4- and 1,3,4-triazole, pyrimidine, 1,3,5-triazine, benzoxazole, benzothiazole, benzimidazole, naphthoxazole, benzo-s-triazole, naphtho-s-triazole, benzo(b)-furan, quinazoline, or quinoxaline radical, B is

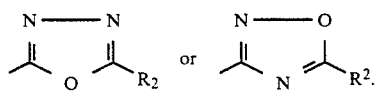

n is 1, 2 or 3, $R_1$ is hydrogen, CN, R, —COR, SO₂R, COOR, CONHR or CON(R')₂, $R_2$ is hydrogen, chlorine, bromine, —OR, —NHR, —N(R')₂ or NHCOR, R' is alkyl having 1 to 6 carbon atoms and being optionally substituted by hydroxyl, C₁-C₄-alkoxy, CN, carboxyl, C₁-C₄-alkoxycarbonyl, CONH₂, chlorine or bromine, or trifluoromethyl, and R is R'', alkenyl having 2 to 5 carbon atoms, phenyl —C₁-C₄-alkyl, phenyl C₁-C₄-alkyl substituted on the phenyl ring by chlorine, methyl and/or methoxy, cyclohexyl optionally substituted by up to three times by methyl and/or chlorine, or phenyl which is optionally substituted by C₁-C₄-alkyl, trifluoromethyl, chlorine, bromine, carboxyl, cyano, C₁-C₄-alkoxycarbonyl and/or C₁-C₄-alkoxy.

2. A compound according to claim 1, wherein B is $$\underset{O}{\overset{N-N}{\underset{\|}{\bigwedge}}}R_2 \quad \text{or} \quad \underset{N}{\overset{N-O}{\underset{\|}{\bigwedge}}}R^2.$$

3. A compound according to claim 1, wherein B is

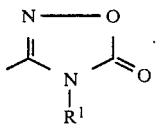

4. A compound according to claim 1, wherein n is 1 to 2.

5. A compound according to claim 1, wherein A is

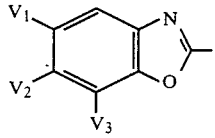

, and
B is

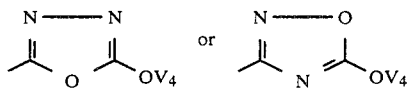

n=1 and
wherein
$V_1$ is hydrogen,
$V_2$ is hydrogen,
$V_3$ is hydrogen, and
$V_4$ is $C_1$–$C_6$-alkyl which is optionally substituted by $C_1$–$C_4$-alkoxy, hydroxyl, chlorine, or cyano; cyclohexyl optionally substituted by up to three times by methyl and/or chlorine; or phenyl-$C_1$–$C_4$-alkyl optionally substituted on the phenyl ring by chlorine, methyl and/or methoxy, or phenyl which is optionally substituted by $C_1$–$C_4$-alkyl, trifluoromethyl, chlorine, bromine, carboxyl, cyano, $C_1$–$C_4$-alkoxy carbonyl and/or $C_1$–$C_4$-alkloxy.

6. A compound according to claim 1, wherein A is benzoxazol-2-yl or benzo-s-triazol-2-yl.

7. A compound according to claim 1, of the formula

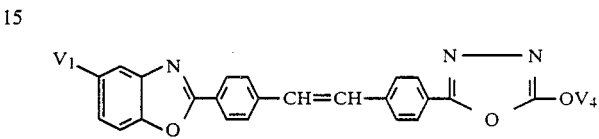

wherein
$V_1$ is hydrogen, and
$V_4$ methyl, ethyl, n-propyl, isopropyl or n-butyl.

8. A compound according to claim 1, of the formula

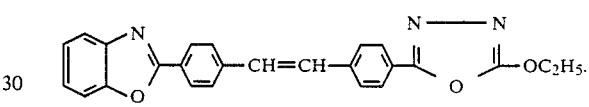

* * * * *

UNITED STATES PATENT AND TRADEMARK OFFICE
CERTIFICATE OF CORRECTION

PATENT NO. : 4,510,311

DATED : April 9, 1985

INVENTOR(S) : Udo Eckstein

It is certified that error appears in the above-identified patent and that said Letters Patent is hereby corrected as shown below:

| | |
|---|---|
| 1st page, Title, line 1 | Correct spelling of "AZOLYLSTYRYL" |
| 1st page, under "U.S. Patent Documents, line 6 | Delete "9/1982" and substitute --9/1978-- |
| 1st Page, Abstract, line 12 | Correct spelling of "cycloalkyl" |
| Col. 3, lines 27, 28 | Correct spelling of "alkoxycarbonyl" |
| Col. 4, line 27 | Before "cf." insert --(-- |
| Col. 6, line 50 | Delete "49/95378" and substitute --49/85378-- |
| Col. 19, "No. 48" in Table, last line under "W" | Delete "-$C_2H_5$" and substitute -- -$C_6H_5$-- |
| Col. 21, line 9 | Correct spelling of "benzoxazole" |
| Col. 22, line 52 | Delete "R" "and substitute --R'-- |

Signed and Sealed this

Seventeenth Day of September 1985

[SEAL]

Attest:

*Attesting Officer*

DONALD J. QUIGG

*Commissioner of Patents and Trademarks—Designate*